United States Patent
Nojiri

(10) Patent No.: US 9,789,031 B2
(45) Date of Patent: Oct. 17, 2017

(54) DENTAL ADHESIVE KIT

(71) Applicant: KURARAY NORITAKE DENTAL INC., Kurashiki-shi (JP)

(72) Inventor: Yamato Nojiri, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 15/027,909

(22) PCT Filed: Oct. 6, 2014

(86) PCT No.: PCT/JP2014/005086
§ 371 (c)(1),
(2) Date: Apr. 7, 2016

(87) PCT Pub. No.: WO2015/052913
PCT Pub. Date: Apr. 16, 2015

(65) Prior Publication Data
US 2016/0235631 A1  Aug. 18, 2016

(30) Foreign Application Priority Data
Oct. 10, 2013  (JP) .................... 2013-212991

(51) Int. Cl.
*A61K 6/083* (2006.01)
*A61K 6/00* (2006.01)

(52) U.S. Cl.
CPC .......... *A61K 6/0023* (2013.01); *A61K 6/0008* (2013.01); *A61K 6/0052* (2013.01)

(58) Field of Classification Search
CPC ........................ A61K 6/0047; A61K 6/0052
See application file for complete search history.

(56) References Cited

U.S. PATENT DOCUMENTS

| | | | |
|---|---|---|---|
| 4,719,297 A | 1/1988 | Henne et al. | |
| 4,826,888 A * | 5/1989 | Sasaki | G03F 7/031 522/103 |
| 6,355,704 B1 | 3/2002 | Nakatsuka et al. | |
| 7,091,258 B2 | 8/2006 | Neubert et al. | |
| 9,125,802 B2 | 9/2015 | Sugiura et al. | |
| 2002/0035169 A1 * | 3/2002 | Nakatsuka | A61K 6/0023 523/116 |
| 2009/0118389 A1 | 5/2009 | Abuelyaman et al. | |
| 2011/0124763 A1 | 5/2011 | Hinamoto et al. | |
| 2012/0196952 A1 * | 8/2012 | Suzuki | A61K 6/0023 523/116 |

FOREIGN PATENT DOCUMENTS

| | | |
|---|---|---|
| EP | 0 009 348 B1 | 7/1983 |
| JP | 57-197289 A | 12/1982 |
| JP | 9-3109 A | 1/1997 |
| JP | 10-245525 A | 9/1998 |
| JP | 2000-16911 A | 1/2000 |
| JP | 2000-159621 A | 6/2000 |
| JP | 2000-212015 A | 8/2000 |
| JP | 2002-256010 A | 9/2002 |
| JP | 2003-96122 A | 4/2003 |
| JP | 2004-231913 A | 8/2004 |
| JP | 2008-540542 A | 11/2008 |
| WO | 2006/122074 A1 | 11/2006 |
| WO | 2010/008077 A1 | 1/2010 |
| WO | 2012/086189 A1 | 6/2012 |

OTHER PUBLICATIONS

International Search Report dated Dec. 9, 2014 in PCT/JP2014/005086 Filed Oct. 6, 2014.

* cited by examiner

*Primary Examiner* — Michael Pepitone
(74) *Attorney, Agent, or Firm* — Oblon, McClelland, Maier & Neustadt, L.L.P.

(57) ABSTRACT

The present invention provides a dental adhesive kit including a bonding material that has a good state stability, that has a good balance between photocurability for LED light irradiation and stability to ambient light, and that is capable of exhibiting high bond strengths to both enamel and dentin with small variability even when subjected to photocuring with a high-power LED irradiation device. The present invention relates to a dental adhesive kit including a primer and a bonding material. The primer includes an acid group-containing monomer, a hydrophilic monomer, and water, and the bonding material includes a hydrophilic monomer (B-1), an aromatic bifunctional monomer (B-2), an aliphatic bifunctional monomer (B-3), α-diketone (B-4), (bis)acylphosphine oxide (B-5), and a benzotriazole compound (B-6) as defined in the description. The content of (B-4) is 0.6 to 2 parts by weight per part by weight of (B-5), and the content of (B-6) is 0.01 to 3 parts by weight per 100 parts by weight of (B-3).

20 Claims, No Drawings

DENTAL ADHESIVE KIT

CROSS REFERENCE TO RELATED APPLICATIONS

This application is a National Stage of International Application No. PCT/JP2014/005086, filed Oct. 6, 2014, the disclosure of which is incorporated herein by reference in its entirety. This application claims priority to Japanese Application Number 2013-212991, filed Oct. 10, 2013.

TECHNICAL FIELD

The present invention relates to a dental adhesive kit including a dental primer and a dental bonding material. The present invention particularly relates to a dental adhesive kit used for bonding between a tooth hard tissue (tooth structure) and a dental restorative material such as a dental composite resin, dental compomer, or dental resin cement.

BACKGROUND ART

Restoration of tooth structures (enamel, dentin, and cementum) damaged, for example, by dental caries typically uses a restorative filling material such as a filling composite resin or filling compomer or a crown restoration material such as a metal alloy, porcelain, or resin material. In general, however, restorative filling materials and crown restoration materials (both of these materials may collectively be referred to as "dental restorative material(s)" in the present description) themselves have no bonding ability to tooth structures. This is why bonding between tooth structures and dental restorative materials conventionally employs various adhesive systems involving the use of adhesives. An example of conventionally-employed adhesive systems is an adhesive system of the so-called etching-type, the use of which consists of subjecting the surface of a tooth structure to an etching treatment with an acid etching agent such as an aqueous phosphoric acid solution, then applying a bonding material which is an adhesive to the tooth structure, and bonding a dental restorative material to the tooth structure.

In recent years, adhesive systems of the so-called self-etching type, which involve no use of any acid etching agent, have been widely employed. Such adhesive systems include: a two-step adhesive system the use of which consists of applying a self-etching primer containing an acidic monomer, a hydrophilic monomer, and water to the surface of a tooth structure and then applying a bonding material containing a crosslinkable monomer and a polymerization initiator to the tooth structure without washing with water; and a one-step adhesive system involving the use of a one-part dental adhesive (one-part bonding material) having functions of both a self-etching primer and a bonding material.

The use of the two-step adhesive system typically consists of applying and drying a primer on a part to be repaired, then applying a bonding material to the part, and causing photocuring. Thus, the two-step adhesive system involves the use of a photopolymerization initiator. Patent Literature 1 discloses that using an acylphosphine oxide compound as a photopolymerization initiator in a bonding material of a two-step adhesive system allows quick, strong hardening and leads to high strength and durability of bond to a tooth structure even when the primer contains no photopolymerization initiator. Also, Patent Literature 2 discloses that using a combination of an acylphosphine oxide compound with an α-diketone compound as a photopolymerization initiator in a bonding material of a two-step adhesive system allows quick, strong hardening and leads to high strength and durability of bond to a tooth structure even when the primer contains no photopolymerization initiator. Examples of Patent Literature 2 present a result indicating that the addition of an α-diketone compound provides an increase in bond durability. However, the use of a photopolymerization initiator that induces quick hardening may disadvantageously cause shortening of allowable operation time since the bonding material containing such a photopolymerization initiator may have too high light sensitivity and hence low stability to ambient light such as light from a fluorescent lamp or digital lamp in a dental office. Thus, a bonding material containing a photopolymerization initiator is required to have a good balance between two conflicting properties, ambient light stability and photocurability. In view of ambient light stability and photocurability, paragraph 0028 of Patent Literature 2 discloses using 0.01 to 0.5 parts by weight of the α-diketone compound per part by weight of the acylphosphine oxide compound.

Halogen irradiation devices have been conventionally used as dental irradiation devices. In recent years, however, LED irradiation devices, which are characterized by long lamp life and high light use efficiency, have become increasingly used as an alternative to halogen irradiation devices. A beam of light emitted from an LED irradiation device has a narrower range of wavelengths and a different emission spectrum than a beam of light emitted from a halogen irradiation device, although these beams of light have similar peak wavelengths. A dental photocurable material thus shows different curing behaviors depending on which of an LED irradiation device and a halogen irradiation device is used to cure the material. Over the last few years, the output power of LED irradiation devices has been increasing, and high-power LED irradiation devices that allow shortening of the curing time of photopolymerizable resins have become increasingly widespread.

The two-step adhesive systems disclosed in Patent Literature 1 and 2 mentioned above show good photocurability when subjected to irradiation with a halogen irradiation device that used to be common. The adhesive systems, however, have been found to have a disadvantage for photocuring with an LED irradiation device in that imparting a satisfactory level of ambient light stability leads to a reduction in the rate of photocurability. The adhesive systems have also been found to pose the problem of low level and large variability of bond strengths to enamel and dentin which are obtained by short-time irradiation with a high-power LED irradiation device.

Patent Literature 3 proposes a composition that exhibits high photocurability even when irradiated with an LED irradiation device, the composition including a photopolymerization initiator consisting only of a combination of bisacylphosphine oxide and α-diketone. Patent Literature 3 also discloses that the composition is available as a bonding material.

A study by the present inventors, however, has revealed that the composition of Patent Literature 3 has room for improvement. To be specific, the composition has low ambient light stability, although it shows a high rate of photocuring when irradiated with an LED irradiation device. In particular, the composition has markedly low ambient light stability when used as a bonding material in a two-step adhesive system.

Patent Literature 4 proposes a photopolymerizable composition having high stability to ambient light, the composition containing α-diketone, acylphosphine oxide, an aromatic tertiary amine, and a benzotriazole compound. Patent Literature 4 discloses that a preferred weight ratio between the α-diketone and the acylphosphine oxide (α-diketone:acylphosphine oxide) is 1:2.5 to 10.

The above composition of Patent Literature 4 is intended for use as a dental restorative material rather than use in a dental adhesive system, and is effectively available as a hydrophobic composition such as a dental composite resin. However, a composition used in a dental adhesive system typically contains a hydrophilic component essential in terms of penetration into collagen of dentin and compatibility with tooth structures. A composition containing both a hydrophilic component and a benzotriazole compound generally has low state stability and suffers deposition of the benzotriazole compound after storage for a short period of time. The composition of Patent Literature 4 is thus difficult to practically use in a dental adhesive system, which fact has been previously known.

CITATION LIST

Patent Literature

Patent Literature 1: JP 2000-16911 A
Patent Literature 2: JP 2000-212015 A
Patent Literature 3: WO 2010/008077 A1
Patent Literature 4: JP 2004-231913 A

SUMMARY OF INVENTION

Technical Problem

The present invention aims to provide a dental adhesive kit including a bonding material that has a good state stability, that has a good balance between photocurability for LED light irradiation and stability to ambient light, and that is capable of exhibiting high bond strengths to both enamel and dentin with small variability even when subjected to photocuring with a high-power LED irradiation device.

Solution to Problem

The present invention is a dental adhesive kit including a dental primer (A) and a dental bonding material (B), wherein the dental primer (A) includes an acid group-containing polymerizable monomer (A-1), a hydrophilic polymerizable monomer (A-2), and water (A-3), the dental bonding material (B) includes a hydrophilic polymerizable monomer (B-1), an aromatic bifunctional polymerizable monomer (B-2), an aliphatic bifunctional polymerizable monomer (B-3), an α-diketone compound (B-4), a (bis)acylphosphine oxide compound (B-5), and a benzotriazole compound (B-6) represented by the formula (1) shown below, a content of the α-diketone compound (B-4) is 0.6 to 2 parts by weight per part by weight of the (bis)acylphosphine oxide compound (B-5), and a content of the benzotriazole compound (B-6) is 0.01 to 3 parts by weight per 100 parts by weight of the aliphatic bifunctional polymerizable monomer (B-3).

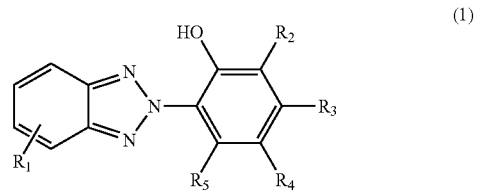

In the formula, $R_1$ is a hydrogen atom, a halogen atom, or an alkyl group having 1 to 6 carbon atoms, and $R_2$ to $R_5$ are each independently a hydrogen atom, a halogen atom, or an organic group having 1 to 12 carbon atoms and optionally containing at least one atom selected from the group consisting of an oxygen atom, a nitrogen atom, a sulfur atom, and a phosphorus atom.

In the present invention, the (bis)acylphosphine oxide compound (B-5) is preferably a bisacylphosphine oxide compound.

In the present invention, a content of the hydrophilic polymerizable monomer (B-1) is preferably 10 to 70 weight %, a content of the aromatic bifunctional polymerizable monomer (B-2) is preferably 10 to 70 weight %, and a content of the aliphatic bifunctional polymerizable monomer (B-3) is preferably 5 to 50 weight %, with respect to the total weight of the dental bonding material (B).

Advantageous Effects of Invention

The present invention provides a dental adhesive kit including a bonding material that has a good state stability, that has a good balance between photocurability for LED light irradiation and stability to ambient light, and that is capable of exhibiting high bond strengths to both enamel and dentin with small variability even when subjected to photocuring with a high-power LED irradiation device.

DESCRIPTION OF EMBODIMENTS

A dental adhesive kit of the present invention includes a dental primer (A) and a dental bonding material (B). The dental primer (A) includes an acid group-containing polymerizable monomer (A-1), a hydrophilic polymerizable monomer (A-2), and water (A-3). The dental bonding material (B) includes a hydrophilic polymerizable monomer (B-1), an aromatic bifunctional polymerizable monomer (B-2), an aliphatic bifunctional polymerizable monomer (B-3), an α-diketone compound (B-4), a (bis)acylphosphine oxide compound (B-5), and a benzotriazole compound (B-6) represented by the formula (1) shown below. The content of the α-diketone compound (B-4) is 0.6 to 2 parts by weight per part by weight of the (bis)acylphosphine oxide compound (B-5), and the content of the benzotriazole compound (B-6) is 0.01 to 3 parts by weight per 100 parts by weight of the aliphatic bifunctional polymerizable monomer (B-3).

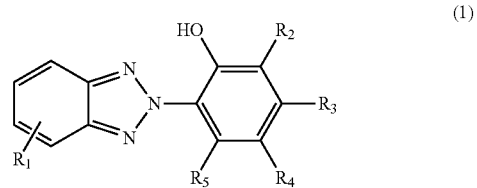

In the formula (1), $R_1$ is a hydrogen atom, a halogen atom, or an alkyl group having 1 to 6 carbon atoms, $R_2$, $R_3$, $R_4$, and $R_5$ are each independently a hydrogen atom, a halogen atom, or an organic group having 1 to 12 carbon atoms and optionally containing at least one atom selected from the group consisting of an oxygen atom, a nitrogen atom, a sulfur atom, and a phosphorus atom.

The benzotriazole compound (B-6) represented by the formula (1) may be one represented by the following formula (2).

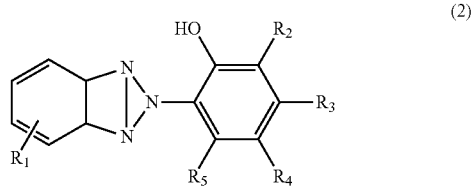

The characters in the formula (2) are the same as those defined in the formula (1).

The components used in the present invention are described in the following paragraphs, in which the dental primer (A) and the dental bonding material (B) are separately discussed.

Dental Primer (A)

The dental primer (A) will first be described in detail.

Acid Group-Containing Polymerizable Monomer (A-1)

The acid group-containing polymerizable monomer (A-1) is a component that has acid-etching effect and priming effect and imparts demineralization ability and penetration ability to the dental primer (A). The acid group-containing polymerizable monomer (A-1) is capable of polymerization and imparts curability to the dental primer (A). The inclusion of the acid group-containing polymerizable monomer (A-1) in the dental primer (A) can contribute to enhancement of bonding ability and bond durability to tooth structures.

An example of the acid group-containing polymerizable monomer (A-1) in the present invention is a polymerizable monomer having at least one of acid groups such as a phosphoric acid group, a pyrophosphoric acid group, a thiophosphoric acid group, a phosphonic acid group, a sulfonic acid group, and a carboxylic acid group and having at least one of polymerizable groups such as an acryloyl group, a methacryloyl group, a vinyl group, and a styrene group. Specific examples of the acid group-containing polymerizable monomer (A-1) are presented below. "Methacryloyl" and "acryloyl" are collectively referred to as "(meth)acryloyl" in the present description.

Examples of the phosphoric acid group-containing polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl] hydrogen phosphate, bis[6-(meth) acryloyloxyhexyl] hydrogen phosphate, bis[8-(meth)acryloyloxyoctyl]hydrogen phosphate, bis[9-(meth)acryloyloxynonyl] hydrogen phosphate, bis[10-(meth)acryloyloxydecyl] hydrogen phosphate, 1,3-di(meth) acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl] hydrogen phosphate; and their acid chlorides, alkali metal salts, and ammonium salts.

Examples of the pyrophosphoric acid group-containing polymerizable monomer include: bis[2-(meth)acryloyloxyethyl] pyrophosphate, bis[4-(meth)acryloyloxybutyl] pyrophosphate, bis[6-(meth)acryloyloxyhexyl]pyrophosphate, bis[8-(meth)acryloyloxyoctyl] pyrophosphate, and bis[10-(meth)acryloyloxydecyl] pyrophosphate; and their acid chlorides, alkali metal salts, and ammonium salts.

Examples of the thiophosphoric acid group-containing polymerizable monomer include: 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, and 20-(meth)acryloyloxyicosyl dihydrogen thiophosphate; and their acid chlorides, alkali metal salts, and ammonium salts.

Examples of the phosphonic acid group-containing polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate; and their acid chlorides, alkali metal salts, and ammonium salts.

Examples of the sulfonic acid group-containing polymerizable monomer include 2-(meth)acrylamido-2-methylpropanesulfonic acid, styrenesulfonic acid, and 2-sulfoethyl (meth)acrylate.

Examples of the carboxylic acid group-containing polymerizable monomer include a polymerizable monomer having one carboxyl group per molecule and a polymerizable monomer having two or more carboxyl groups per molecule.

Examples of the polymerizable monomer having one carboxyl group per molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth) acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and their acid halides.

Examples of the polymerizable monomer having two or more carboxyl groups per molecule include: 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)

acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, and 2-(meth)acryloyloxyethyl-3'-(meth)acryloyloxy-2'-(3,4-dicarboxybenzoyloxy)propyl succinate; and their acid anhydrides and acid halides.

Among these acid group-containing polymerizable monomers, the phosphoric or pyrophosphoric acid group-containing (meth)acrylic monomers are preferable since such monomers provide better bonding ability to tooth structures. Particularly preferred are the phosphoric acid group-containing (meth)acrylic monomers. Among the phosphoric acid group-containing (meth)acrylic monomers, a divalent phosphoric acid group-containing (meth)acrylic monomer that has as the main chain of the molecule an alkyl or alkylene group having 6 to 20 carbon atoms is more preferable, and a divalent phosphoric acid group-containing (meth)acrylic monomer that has as the main chain of the molecule an alkylene group having 8 to 12 carbon atoms, such as 10-methacryloyloxydecyl dihydrogen phosphate, is most preferable.

One monomer may be contained alone as the acid group-containing polymerizable monomer (A-1) or a combination of two or more monomers may be contained as the acid group-containing polymerizable monomers (A-1). Having too high or low a content of the acid group-containing polymerizable monomer (A-1) may cause a decline in bonding ability. Thus, the content of the acid group-containing polymerizable monomer (A-1) is preferably in the range of 1 to 50 weight %, more preferably in the range of 1 to 30 weight %, and most preferably in the range of 3 to 20 weight %, with respect to the total weight of the dental primer (A).

Hydrophilic Polymerizable Monomer (A-2)

In the context of the present invention, the hydrophilic polymerizable monomer (A-2) used in the dental primer (A) refers to a polymerizable monomer, other than the acid group-containing polymerizable monomer (A-1), (i.e., a polymerizable monomer containing no acid group) which has a solubility of 10 weight % or more in water at 25° C. The hydrophilic polymerizable monomer (A-2) preferably has a solubility of 30 weight % or more in water at 25° C., and is more preferably freely soluble in water at 25° C. The hydrophilic polymerizable monomer (A-2) promotes the penetration of the other components of the dental primer (A) into a tooth structure. The monomer (A-2) itself also penetrates into a tooth structure and adheres to an organic component (collagen) in the tooth structure.

Examples of the hydrophilic polymerizable monomer (A-2) include 2-hydroxyethyl (meth)acrylate, 2-hydroxypropyl (meth)acrylate, 3-hydroxypropyl (meth)acrylate, 1,3-dihydroxypropyl (meth)acrylate, 2,3-dihydroxypropyl (meth)acrylate, 2-(trimethylammonium)ethyl (meth)acryl chloride, polyethylene glycol di(meth)acrylate (having nine or more oxyethylene groups), N,N-dimethyl(meth)acrylamide, N,N-diethyl(meth)acrylamide, N,N-di-n-propyl(meth)acrylamide, N-ethyl-N-methyl(meth)acrylamide, N-methylol(meth)acrylamide, N-hydroxyethyl(meth)acrylamide, and N,N-(dihydroxyethyl)(meth)acrylamide. Among these, 2-hydroxyethyl (meth)acrylate, glycerin mono(meth)acrylate, and N,N-diethyl(meth)acrylamide are preferable.

One of the above monomers may be contained alone as the hydrophilic polymerizable monomer (A-2) or a combination of two or more thereof may be contained as the hydrophilic polymerizable monomer (A-2). The content of the hydrophilic polymerizable monomer (A-2) is typically in the range of 0.1 to 95 weight %, preferably in the range of 1 to 70 weight %, and more preferably in the range of 10 to 50 weight %, with respect to the total weight of the dental primer (A).

Water (A-3)

The water (A-3) is a component that contributes to the penetration of the polymerizable monomers into the collagen layer of dentin and that improves the bonding ability and bond durability of the dental primer (A) to tooth structures. The water (A-3) preferably contains no impurities that may have adverse effect, and is preferably distilled water or ion-exchanged water. The water (A-3) is a solvent component in the dental primer (A). The water (A-3) may be used alone as the solvent component in the dental primer (A), or a mixed solvent of the water (A-3) and an organic solvent mentioned later may be used as the solvent component.

The content of the water (A-3) is preferably in the range of 0.01 to 90 weight %, more preferably in the range of 0.1 to 70 weight %, and most preferably in the range of 10 to 60 weight %, with respect to the total weight of the dental primer (A).

In the present invention, the dental primer (A) is applied to a tooth surface, and then dried with a dental air syringe into the form of a very thin layer. Thus, the primer is not necessarily required to contain a polymerization initiator. It is desirable, however, for the dental primer (A) to contain a polymerization initiator, since there may be a reduction in curability and hence a reduction in bond strength if, for example, the practitioner causes an excess amount of the dental primer (A) to remain on the tooth surface after drying of the dental primer (A). The polymerization initiator contained can be a commonly-known photopolymerization initiator and/or a chemical polymerization initiator. For example, α-diketone and a (bis)acylphosphine oxide compound essential for the dental bonding material (B) used in the present invention are suitable for use as the photopolymerization initiator. Other photopolymerization initiators such as thioxanthones, ketals, and coumarin compounds may be used. These polymerization initiators are the same as photopolymerization initiators mentioned as examples for the dental bonding material (B) described later. The dental primer (A) may contain a polymerization accelerator mentioned as an example for the dental bonding material (B) described later.

An example of chemical polymerization initiators that are suitable for use as a polymerization initiator in the present invention is a redox polymerization initiator system composed of an oxidant and a reductant. The use of a redox polymerization initiator system requires the dental primer (A) used in the present invention to be packaged in two or more parts so that the oxidant and the reductant are contained separately from each other. Given that the dental adhesive kit of the present invention necessarily requires the combined use of the dental primer (A) and the dental bonding material (B), adding one of an oxidant and a reductant to the dental bonding material (B) allows the dental primer (A) to contain only the other of the oxidant and the reductant and be packaged in one part.

As the oxidant there can be contained, for example, an organic peroxide such as ketone peroxide, hydroperoxide, diacyl peroxide, dialkyl peroxide, peroxyketal, peroxyester, or peroxydicarbonate. These oxidant components are the same as those mentioned as examples for the dental bonding material (B) described later.

An aromatic tertiary amine, an aliphatic tertiary amine, a sulfinic acid, or a sulfinic acid salt is suitable for use as the reductant. These reductant components are the same as those mentioned as examples for the dental bonding material (B) described later.

One of these polymerization initiators may be contained alone, or a combination of two or more thereof may be contained. The (total) content of the polymerization initiator(s) is typically in the range of 0.01 to 20 weight %, preferably in the range of 0.05 to 10 weight %, and more preferably in the range of 0.1 to 5 weight %, with respect to the total weight of the dental primer (A).

An additional polymerizable monomer other than the acid group-containing polymerizable monomer (A-1) and the hydrophilic polymerizable monomer (A-2) may be used in the dental primer (A) of the present invention where desired. In this case, a commonly-known radically-polymerizable monomer having no acid group, having a solubility less than 10 weight % in water at 25° C., and having a polymerizable unsaturated group can be used as the additional polymerizable monomer without any other limitation. In general, (meth)acrylate-based and (meth)acrylamide-based polymerizable monomers are suitable for use in view of the curing rate and the mechanical properties of the resulting cured product.

A volatile solvent such as ethanol or acetone, a polymerization accelerator, a polymerization inhibitor, a colorant, a fluorescent agent, and an ultraviolet absorber may be added where desired. To impart antibacterial properties, an antibacterial polymerizable monomer having a cationic group, such as (meth)acryloyloxydodecylpyridinium bromide, (meth)acryloyloxyhexadecylpyridinium chloride, or (meth)acryloyloxydecylammonium chloride, may be added. To impart anticariogenicity, a metal fluoride such as sodium fluoride may be added. Furthermore, a filler can be added in an amount which causes no loss in the flowability of the dental primer (A). These components are the same as those mentioned as examples for the dental bonding material (B) described later.

Dental Bonding Material (B)

Next, the dental bonding material (B) will be described in detail.

the range of 10 to 70 weight %, more preferably in the range of 15 to 60 weight %, and most preferably in the range of 20 to 50 weight %, with respect to the total weight of the dental bonding material (B). The content of the hydrophilic polymerizable monomer (B-1) is preferably 100 to 500 parts by weight, more preferably 110 to 400 parts by weight, and even more preferably 120 to 350 parts by weight, per 100 parts by weight of the aliphatic bifunctional polymerizable monomer (B-3) contained in the dental bonding material (B).

Aromatic Bifunctional Polymerizable Monomer (B-2)

The aromatic bifunctional polymerizable monomer (B-2) is a different component from the hydrophilic polymerizable monomer (B-1), and has a solubility less than 10 weight % in water at 25° C. The aromatic bifunctional polymerizable monomer (B-2) has no acid group. The aromatic bifunctional polymerizable monomer (B-2) improves the characteristics such as mechanical strength and handling properties of the dental bonding material (B).

Examples of the aromatic bifunctional polymerizable monomer (B-2) include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and a bisphenol A compound represented by the following formula (A) (a commercially-available example is "EPOXY ESTER 3002M" (trade name), a methacrylic acid adduct of 2 mole propylene oxide adduct of bisphenol A diglycidyl ether, manufactured by Kyoeisha Chemical Co., Ltd):

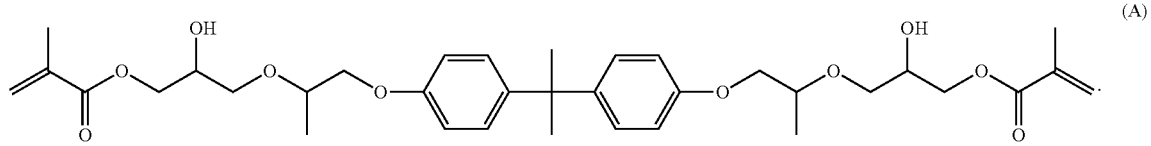 [SMILES: C=C(C)C(=O)OCC(O)COC(C)COc1ccc(C(C)(C)c2ccc(OCC(C)OCC(O)COC(=O)C(=C)C)cc2)cc1]

(A)

Hydrophilic Polymerizable Monomer (B-1)

Polymerizable monomers that can be used as the hydrophilic polymerizable monomer (B-1) of the dental bonding material (B) in the present invention are the same as those mentioned as examples of the hydrophilic polymerizable monomer (A-2) of the dental primer (A). Among the polymerizable monomers, 2-hydroxyethyl (meth)acrylate, glycerin mono(meth)acrylate, and N,N-diethyl(meth)acrylamide are preferable in view of the penetration into the collagen layer of dentin.

One of these monomers may be used alone as the hydrophilic polymerizable monomers (B-1) or a combination of two or more thereof may be used as the hydrophilic polymerizable monomers (B-1). In general, the content of the hydrophilic polymerizable monomer (B-1) is preferably in Preferred among these are 2,2-bis[4-(3-methacryloyloxy-2-hydroxypropoxy)phenyl]propane and the bisphenol A compound represented by the formula (A). Most preferred is 2,2-bis[4-(3-methacryloyloxy-2-hydroxypropoxy)phenyl]propane.

One of the above monomers may be used alone as the aromatic bifunctional polymerizable monomer (B-2) or a combination of two or more thereof may be used as the aromatic bifunctional polymerizable monomer (B-2). In general, the content of the aromatic bifunctional polymerizable monomer (B-2) is preferably in the range of 10 to 70 weight %, more preferably in the range of 15 to 60 weight %, and most preferably in the range of 20 to 50 weight %, with respect to the total weight of the dental bonding material (B).

Aliphatic Bifunctional Polymerizable Monomer (B-3)

The aliphatic bifunctional polymerizable monomer (B-3) is a different component from the hydrophilic polymerizable monomer (B-1), and has a solubility less than 10 weight % in water at 25° C. The aliphatic bifunctional polymerizable monomer (B-3) has no acid group. The aliphatic bifunctional polymerizable monomer (B-3) improves the characteristics such as mechanical strength and handling properties of the dental bonding material (B), and contributes to the dissolution of the benzotriazole compound (B-6) in the dental bonding material (B).

Examples of the aliphatic bifunctional polymerizable monomer (B-3) include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1, 10-decanediol di(meth)acrylate, 1,2-bis(3-methacryloyloxy-2-hydroxypropyloxy)ethane, and 2,2,4-trimethylhexamethylene bis(2-carbamoyloxyethyl) di(meth)acrylate. Among these, neopentyl glycol di(meth)acrylate, triethylene glycol di(meth)acrylate, 1,6-hexanediol di(meth)acrylate, 1,10-decanediol di(meth)acrylate are preferable, and neopentyl glycol di(meth)acrylate is most preferable, in view of the dissolution of the benzotriazole compound (B-6).

One of the above monomers may be used alone as the aliphatic bifunctional polymerizable monomer (B-3) or a combination of two or more thereof may be used as the aliphatic bifunctional polymerizable monomer (B-3). In general, the content of the polymerizable monomer is preferably in the range of 5 to 50 weight %, more preferably in the range of 7 to 45 weight %, and most preferably in the range of 10 to 40 weight %, with respect to the total weight of the dental bonding material (B).

A tri- or higher-functional polymerizable monomer having a solubility less than 10 weight % in water at 25° C. and having no acid group can be used in the dental bonding material (B) of the present invention where desired. Examples of the tri- or higher-functional polymerizable monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth) acrylate, dipentaerythritol tetra(meth)acrylate, dipentaerythritol penta(meth)acrylate, N,N-(2,2,4-trimethylhexamethylene)-bis[2-(aminocarboxy)propane-1,3-diol]tetramethacrylate, and 1,7-diacryloyloxy-2,2,6,6-tetraacryloyloxymethyl-4-oxyheptane.

An acid group-containing polymerizable monomer is not an essential component that the dental bonding material (B) needs to contain in order to have a sufficient bonding ability to tooth structures and restorative materials. It is desirable, however, for the dental bonding material (B) to contain an acid group-containing polymerizable monomer in order to further enhance the bonding ability. Monomers usable as such an acid group-containing polymerizable monomer are the same as those usable as the acid group-containing polymerizable monomer (A-1) in the dental primer (A) of the present invention. In particular, the dental bonding material (B) containing a phosphoric acid group-containing polymerizable monomer is preferable because of its excellence in bond strength to tooth structures or restorative materials such as a metal, resin, and porcelain. The (total) content of the acid group-containing polymerizable monomer(s) used is typically in the range of 0.1 to 50 weight % and preferably in the range of 1 to 30 weight %, with respect to the total weight of the dental bonding material (B).

α-Diketone (B-4)

The α-diketone (B-4) functions as a photopolymerization initiator. Examples of the α-diketone (B-4) used in the present invention include diacetyl, dibenzyl, camphorquinone, 2,3-pentadione, 2,3-octadione, 9,10-phenanthrenequinone, 4,4'-oxybenzyl, and acenaphthenequinone. Particularly preferred among these is camphorquinone, since it shows maximum absorption at a wavelength in the visible region. One α-diketone (B-4) may be contained alone or a combination of two or more α-diketones (B-4) may be contained.

(Bis)Acylphosphine Oxide (B-5)

The dental bonding material (B) used in the present invention further contains the (bis)acylphosphine oxide compound (B-5) as a photopolymerization initiator. The dental bonding material (B) can have increased photocurability and yield high bond strength by virtue of containing the (bis)acylphosphine oxide compound (B-5). Bisacylphosphine oxide and acylphosphine oxide are collectively referred to as "(bis)acylphosphine oxide" in the present description.

Examples of the (bis)acylphosphine oxide compound (B-5) used in the present invention include an acylphosphine oxide, a bisacylphosphine oxide, and a water-soluble acylphosphine oxide.

Examples of the acylphosphine oxide used as the (bis) acylphosphine oxide compound (B-5) include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl) phosphonate.

Examples of the bisacylphosphine oxide include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

The water-soluble acylphosphine oxide preferably has an alkali metal ion, an alkaline earth metal ion, a pyridinium ion, or an ammonium ion in the acylphosphine oxide molecule. For example, the water-soluble acylphosphine oxide can be synthesized by a method disclosed in EP 0009348 B1 or JP 57-197289 A.

Specific examples of the water-soluble acylphosphine oxide include sodium monomethyl acetylphosphonate, sodium monomethyl (1-oxopropyl)phosphonate, sodium monomethyl benzoylphosphonate, sodium monomethyl (1-oxobutyl)phosphonate, sodium monomethyl (2-methyl-1-oxopropyl)phosphonate, sodium acetylphosphonate, sodium monomethyl acetylphosphonate, sodium acetylmethylphosphonate, methyl 4-(hydroxymethoxyphosphinyl)-4-oxobutanoate sodium salt, methyl-4-oxo-phosphonobutanoate monosodium salt, acetylphenylphosphinate sodium salt, sodium (1-oxopropyl)pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-dimethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl (2-methyl-1,3-thiazolidin-2-yl)phosphonate sodium salt, (2-methylperhydro-1,3-diazin-2-yl)phosphonite sodium salt, acetylphosphinate sodium salt, (1,1-diethoxyethyl) phosphonite sodium salt, (1,1-diethoxyethyl)methylphosphonite sodium salt, methyl(2-methyloxathiolan-2-yl)phosphinate sodium salt, methyl(2,4,5-trimethyl-1,3-dioxolan-2-yl)phosphinate sodium salt, methyl(1,1-propoxyethyl) phosphinate sodium salt, (1-methoxyvinyl) methylphosphinate sodium salt, (1-ethylthiovinyl) methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxyme sodium salt, 1-[(N-ethoxyimino)ethyl]methylphosphinate sodium salt, methyl(1-phenyliminoethyl)phosphinate sodium salt, methyl(1-phenylhydrazonoethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methylphosphinate sodium salt, formylmethylphosphinate sodium salt, (1,1-dimethoxypropyl)methylphosphinate sodium salt, methyl(1-oxopropyl)phosphinate sodium salt, (1,1-dimethoxypropyl)methylphosphinate dodecylguanidine salt, (1,1-dimethoxypropyl) methylphosphinate isopropylamine salt, acetylmethylphosphinate thiosemicarbazone sodium salt, 1,3,5-tributyl-4-methylamino-1,2,4-triazolium(1,1-dimethoxyethyl)-methylphosphinate, 1-butyl-4-butylaminomethylamino-3,5-dipropyl-1,2,4-triazolium(1,1-dimethoxyethyl)-methylphosphinate, 2,4,6-trimethylbenzoylphenylphosphine oxide sodium salt, 2,4,6-trimethylbenzoylphenylphosphine oxide potassium salt, and 2,4,6-trimethylbenzoylphenylphosphine oxide ammonium salt. Examples of the water-soluble acylphosphine oxide further include compounds as specified in JP 2000-159621 A.

Among these acylphosphine oxides, bisacylphosphine oxides, and water-soluble acylphosphine oxides, 2,4,6-trimethylbenzoyldiphenylphosphine oxide, 2,4,6-trimethylbenzoylmethoxyphenylphosphine oxide, 2,4,6-trimethylbenzoylphenylphosphine oxide sodium salt, and bisacylphosphine oxides are preferable. Bisacylphosphine oxides are more preferable, and bis(2,4,6-trimethylbenzoyl)phenylphosphine oxide is most preferable. One (bis)acylphosphine oxide compound (B-5) may be used alone, or two or more (bis) acylphosphine oxide compounds (B-5) may be used in combination as necessary.

In view of, for example, the curability of the dental bonding material (B), it is recommendable to adjust the contents of the α-diketone (B-4) and the (bis)acylphosphine oxide compound (B-5) so that the total content of the (bis)acylphosphine oxide compound (B-5) and the α-diketone (B-4) is typically 0.5 to 5 weight %, preferably 0.7 to 4 weight %, and more preferably 1 to 3 weight %, with respect to the total weight of the dental bonding material (B).

To be more specific, 0.6 to 2 parts by weight of the α-diketone (B-4) may be contained per part by weight of the (bis)acylphosphine oxide compound (B-5). In this case, the dental bonding material (B) shows high curability when subjected to LED light irradiation, and constantly exhibits good bonding ability with small variability in bond strength even when irradiated with a high-power LED irradiation device. The α-diketone (B-4) is contained preferably in an amount of 0.6 to 1.5 parts by weight and more preferably in an amount of 0.6 to 1.2 parts by weight.

A tertiary amine can be used as a polymerization accelerator in the dental bonding material (B) where desired. The tertiary amine used in the present invention may be an aliphatic amine or an aromatic amine.

Examples of the aliphatic tertiary amine include N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, 2-(dimethylamino)ethyl methacrylate and triethanolamine are more preferably used in view of the curability and storage stability of the dental bonding material (B).

Examples of the aromatic amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, n-butoxyethyl N,N-dimethylaminobenzoate, 2-(methacryloyloxy)ethyl 4-N,N-dimethylaminobenzoate, 4-N,N-dimethylaminobenzophenone, and butyl 4-dimethylaminobenzoate. Among these, at least one selected from the group consisting of N,N-di(2-hydroxyethyl)-p-toluidine, ethyl 4-(N,N-dimethylamino)benzoate, n-butoxyethyl N,N-dimethylaminobenzoate, and 4-N,N-dimethylaminobenzophenone is preferably used in view of their ability to impart high curability to the dental bonding material (B). One tertiary amine may be contained alone or a combination of two or more tertiary amines may be contained.

The (total) content of the tertiary amine(s) used is preferably in the range of 0.05 to 10 weight %, more preferably in the range of 0.1 to 7 weight %, and even more preferably in the range of 0.5 to 5 weight %, with respect to the total weight of the dental bonding material (B).

Benzotriazole Compound (B-6)

The benzotriazole compound (B-6) functions as a stabilizer against ambient light. The benzotriazole compound (B-6) has a structure represented by the formula (1).

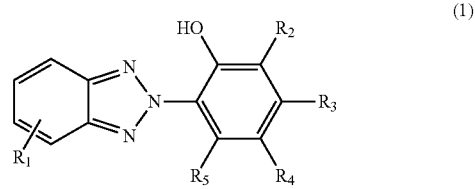

In the formula (1), $R_1$ is a hydrogen atom, a halogen atom, or an alkyl group having 1 to 6 carbon atoms, and $R_2$ to $R_5$ are each independently a hydrogen atom, a halogen atom, or an organic group having 1 to 12 carbon atoms and optionally containing at least one atom selected from the group consisting of an oxygen atom, a nitrogen atom, a sulfur atom, and a phosphorus atom.

Examples of the halogen atom denoted by $R_1$ to $R_5$ include a fluorine atom, a chlorine atom, a bromine atom, and an iodine atom. Preferred is a chlorine atom.

The alkyl group denoted by $R_1$ which has 1 to 6 carbon atoms may be linear, branched, or cyclic. Examples of the alkyl group include methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, isohexyl, and cyclohexyl groups.

The organic group denoted by $R_2$ to $R_5$ which has 1 to 12 carbon atoms and which optionally contains at least one atom selected from the group consisting of an oxygen atom, a nitrogen atom, a sulfur atom, and a phosphorus atom may be aliphatic or aromatic and may be saturated or unsaturated. The organic group may have a branched structure and may have a cyclic structure. Examples of the organic group having 1 to 12 carbon atoms include a hydrocarbon group having 1 to 12 carbon atoms. The hydrocarbon group may be substituted with one selected from the group consisting of a hydroxyl group, an amino group, and a mercapto group, may contain, for example, —O—, —S—, or —NH— interposed between carbon atoms, may contain, for example, an nitrogen atom or —P(=O)— interposed between carbon atoms and serving as a branching point from which a branch originates, and may have a heterocyclic structure containing an oxygen atom, a nitrogen atom, a sulfur atom, and/or a phosphorus atom.

Examples of the hydrocarbon group include alkyl, alkenyl, alkynyl, aryl, alkylaryl, arylalkyl, alkylarylalkyl, and alkenylaryl groups.

The benzotriazole compound (B-6) is preferably a compound having the structure represented by the formula (1), where $R_1$ is a hydrogen atom or a chlorine atom present at position 5 on the benzotriazole structure, $R_3$ and $R_5$ are each a hydrogen atom, and at least either $R_2$ or $R_4$ is a hydrocarbon group having 1 to 12 carbon atoms ($R_2$ and $R_4$ may be the same or different when each of them is a hydrocarbon group having 1 to 12 carbon atoms). More preferably, $R_2$ and $R_4$ are each independently a linear or branched alkyl group having 1 to 12 carbon atoms or a phenylalkyl group having 7 to 12 carbon atoms.

Examples of the linear or branched alkyl group having 1 to 12 carbon atoms include methyl, ethyl, n-propyl, isopropyl, n-butyl, isobutyl, sec-butyl, tert-butyl, n-pentyl, isopentyl, neopentyl, tert-pentyl, n-hexyl, isohexyl, tert-hexyl, n-heptyl, tert-heptyl, n-octyl, 2-ethylhexyl, tert-octyl, n-nonyl, n-decyl, n-undecyl, and n-dodecyl groups.

Examples of the phenylalkyl group having 7 to 12 carbon atoms include benzyl, α,α-dimethylbenzyl, and phenethyl groups.

Specific exemplary compounds particularly preferred as the benzotriazole compound (B-6) are shown below.

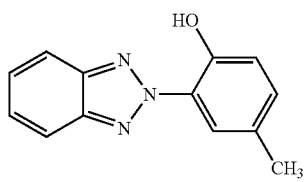

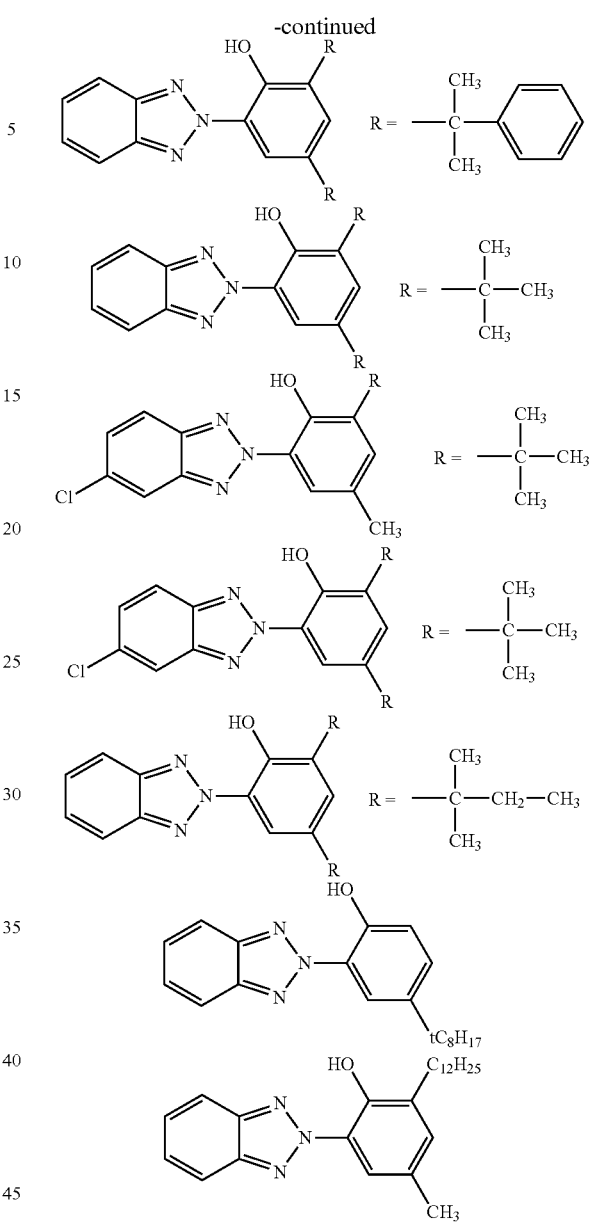

In view of the dissolution in the dental bonding material (B), the content of the benzotriazole compound (B-6) is 0.01 to 3 parts by weight, preferably 0.05 to 2.5 parts by weight, and more preferably 0.1 to 2 parts by weight, per 100 parts by weight of the aliphatic bifunctional polymerizable monomer (B-3). The content of the benzotriazole compound (B-6) is 0.005 to 1.7 parts by weight, preferably 0.01 to 1.6 parts by weight, more preferably 0.1 to 1.5 parts by weight, and particularly preferably 0.3 to 1.3 parts by weight, per 100 parts by weight of the hydrophilic polymerizable monomer (B-1).

In view of the curability, the dental bonding material (B) may contain a polymerization initiator other than the α-diketone (B-4) and the (bis)acylphosphine oxide compound (B-5). The polymerization initiator used can be a commonly-known polymerization initiator. In particular, one polymerization initiator for photopolymerization or chemical polymerization is used alone or two or more polymerization initiators for photopolymerization or chemical polymerization are used in appropriate combination.

Examples of the photopolymerization initiator include thioxanthones, quaternary ammonium salts of thioxanthones, ketals, coumarins, benzoin alkyl ether compounds, and α-aminoketone compounds.

Examples of the thioxanthones and the quaternary ammonium salts of thioxanthones that may be used as the photopolymerization initiator include thioxanthone, 2-chlorothioxanthen-9-one, 2-hydroxy-3-(9-oxo-9H-thioxanthen-4-yloxy)-N,N,N-trimethyl-propanaminium chloride, 2-hydroxy-3-(1-methyl-9-oxo-9H-thioxanthen-4-yloxy)-N,N,N-trimethyl-propanaminium chloride, 2-hydroxy-3-(9-oxo-9H-thioxanthen-2-yloxy)-N,N,N-trimethyl-propanaminium chloride, 2-hydroxy-3-(3,4-dimethyl-9-oxo-9H-thioxanthen-2-yloxy)-N,N,N-trimethyl-1-propan aminium chloride, 2-hydroxy-3-(3,4-dimethyl-9H-thioxanthen-2-yloxy)-N,N,N-trimethyl-1-propanaminium chloride, and 2-hydroxy-3-(1,3,4-trimethyl-9-oxo-9H-thioxanthen-2-yloxy)-N,N,N-trimethyl-1-propanaminium chloride.

A particularly preferred thioxanthone among the above-mentioned thioxanthones is 2-chlorothioxanthen-9-one, and a particularly preferred quaternary ammonium salt of a thioxanthone among the above-mentioned quaternary ammonium salts of thioxanthones is 2-hydroxy-3-(3,4-dimethyl-9H-thioxanthen-2-yloxy)-N,N,N-trimethyl-1-propanaminium chloride.

Examples of the ketals that may be used as the photopolymerization initiator include benzyl dimethyl ketal and benzyl diethyl ketal.

Examples of the coumarin compounds that may be used as the photopolymerization initiator include compounds disclosed in JP 9-3109 A and JP 10-245525 A, such as 3,3'-carbonylbis(7-diethylaminocoumarin), 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphto[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazoyl)-2,3,6,7-tetrahydro-1,1,7,7-tetramethyl-1H,5H,11H-[1]benzopyrano[6,7,8-ij]quinolizin-11-one.

Among the above coumarin compounds, 3,3'-carbonylbis(7-diethylaminocoumarin) and 3,3'-carbonylbis(7-dibutylaminocoumarin) are particularly preferable.

Examples of the benzoin alkyl ethers that may be used as the photopolymerization initiator include benzoin methyl ether, benzoin ethyl ether, benzoin isopropyl ether, and benzoin isobutyl ether.

Examples of the α-aminoketones that may be used as the photopolymerization initiator include 2-methyl-1-[4-(methylthio)phenyl]-2-morpholinopropan-1-one.

An organic peroxide is preferably used as the chemical polymerization initiator in the present invention. The organic peroxide used as the chemical polymerization initiator is not particularly limited, and can be a commonly-known organic peroxide. Typical examples of the organic peroxide include ketone peroxides, hydroperoxides, diacyl peroxides, dialkyl peroxides, peroxyketals, peroxyesters, and peroxydicarbonates.

Examples of the ketone peroxides that may be used as the chemical polymerization initiator include methyl ethyl ketone peroxide, methyl isobutyl ketone peroxide, methylcyclohexanone peroxide, and cyclohexanone peroxide.

Examples of the hydroperoxides that may be used as the chemical polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides that may be used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides that may be used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexine.

Examples of the peroxyketals that may be used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxyesters that may be used as the chemical polymerization initiator include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleic acid.

Examples of the peroxydicarbonates that may be used as the chemical polymerization initiator include di-3-methoxy peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, the diacyl peroxides are preferably used in view of the overall balance of safety, storage stability, and radical formation potential. Among the diacyl peroxides, benzoyl peroxide is particularly preferably used.

In view of the curability, the dental bonding material (B) of the present invention may contain a polymerization accelerator other than the tertiary amine. The polymerization accelerator used in the present invention can be a commonly-known polymerization accelerator. One polymerization accelerator may be used alone or two or more polymerization accelerators may be used in appropriate combination.

Examples of the polymerization accelerator include primary and secondary amines, sulfinic acids, sulfinates, borate compounds, barbituric acid derivatives, triazine compounds, copper compounds, tin compounds, vanadium compounds, halogen compounds, aldehydes, thiol compounds, sulfites, hydrogen sulfites, and thiourea compounds.

Examples of the primary and secondary amines include: primary amines such as n-butylamine, n-hexylamine, and n-octylamine; secondary amines such as diisopropylamine, dibutylamine, and N-methylethanolamine.

Examples of the sulfinic acids and sulfinates that may be used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred are sodium benzenesulfinate, sodium p-toluenesulfinate, and sodium 2,4,6-triisopropylbenzenesulfinate.

The borate compound used as the polymerization accelerator is preferably an aryl borate compound. Specific examples of aryl borate compounds that are suitable for use as the polymerization accelerator include borate compounds having one aryl group per molecule, such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts of trialkylphenylboron, trialkyl(p-chlorophenyl)boron, trialkyl(p-fluorophenyl)boron, trialkyl[(3,5-bistrifluoromethyl)phenylboron], trialkyl[3, 5-bis(1,1,1,3,3,3-hexafluoro-2-methoxy-2-propyl)phenyl]boron, trialkyl(p-nitrophenyl) boron, trialkyl(m-nitrophenyl)boron, trialkyl(p-butylphenyl)boron, trialkyl(m-butylphenyl)boron, trialkyl (p-butyloxyphenyl)boron, trialkyl(m-butyloxyphenyl) boron, trialkyl(p-octyloxyphenyl)boron, and trialkyl(m-octyloxyphenyl)boron (their alkyl groups are each at least one selected from the group consisting of, for example, an n-butyl group, an n-octyl group, and an n-dodecyl group).

Examples of the borate compound include those that have two aryl groups per molecule, such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts of dialkyldiphenylboron, dialkyldi(p-chlorophenyl)boron, dialkyldi(p-fluorophenyl)boron, dialkyl[di(3,5-bis-trifluoromethyl)phenyl]boron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi (p-octyloxyphenyl)boron, and dialkyldi(m-octyloxyphenyl) boron (their alkyl groups are each at least one selected from the group consisting of, for example, an n-butyl group, an n-octyl group, and an n-dodecyl group).

Examples of the borate compound further include those that have three aryl groups per molecule, such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts of monoalkyltriphenylboron, monoalkyltri(p-chlorophenyl)boron, monoalkyltri(p-fluorophenyl)boron, monoalkyltri(3,5-bistrifluoromethyl)phenylboron, monoalkyltri[3,5-bis(1,1,1,3, 3,3-hexafluoro-2-methoxy-2-propyl)phenyl]boron, monoalkyltri(p-nitrophenyl)boron, monoalkyltri(m-nitrophenyl) boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl) boron (their alkyl groups are each at least one selected from, for example, an n-butyl group, an n-octyl group, and an n-dodecyl group).

Examples of the borate compound further include those that have four aryl groups per molecule, such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts of tetraphenylboron, tetrakis(p-chlorophenyl)boron, tetrakis(p-fluorophenyl)boron, tetrakis[(3,5-bistrifluoromethyl)phenyl] boron, tetrakis[3,5-bis(1,1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl) boron, tetrakis(m-butyloxyphenyl)boron, tetrakis(p-octyloxyphenyl)boron, tetrakis(m-octyloxyphenyl)boron, (p-fluorophenyl)triphenylboron, (3,5-bistrifluoromethylphenyl) triphenylboron, (p-nitrophenyl)triphenylboron, (m-butyloxyphenyl)triphenylboron, (p-butyloxyphenyl)triphenylboron, (m-octyloxyphenyl)triphenylboron, and (p-octyloxyphenyl)triphenylboron.

In view of storage stability, it is more preferable to use the borate compounds having three or four aryl groups per molecule among the above aryl borate compounds. One of these aryl borate compounds may be used alone or a mixture of two or more thereof may be used.

Examples of the barbituric acid derivatives that may be used as the polymerization accelerator include: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5- butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids; and salts of the barbituric acids (alkali metal salts and alkaline earth metal salts are particularly preferable). Examples of the salts of the barbituric acids include sodium 5-butylbarbiturate, sodium 1,3,5-trimethylbarbiturate, and sodium 1-cyclohexyl-5-ethylbarbiturate.

Examples of particularly preferred barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compounds that may be used as the polymerization accelerator include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Among the triazine compounds mentioned above as examples, 2,4,6-tris(trichloromethyl)-s-triazine is particularly preferable in terms of polymerization activity. In terms of storage stability, 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine are particularly preferable. The above triazine compounds may be used alone or a mixture of two or more thereof may be used.

Examples of the copper compounds that are suitable for use as the polymerization accelerator include copper acetylacetonate, copper (II) acetate, copper oleate, copper (II) chloride, and copper (II) bromide.

Examples of the tin compounds that may be used as the polymerization accelerator include di-n-butyltin dimaleate, di-n-octyltin dimaleate, di-n-octyltin dilaurate, and di-n-butyltin dilaurate. Particularly preferred tin compounds are di-n-octyltin dilaurate and di-n-butyltin dilaurate.

The vanadium compound used as the polymerization accelerator is preferably a compound of tetravalent and/or pentavalent vanadium. Examples of the compound of tetravalent and/or pentavalent vanadium include compounds mentioned in JP 2003-96122 A, such as divanadium (IV) tetroxide, vanadium (IV) oxide acetylacetonate, vanadyl (IV) oxalate, vanadyl (IV) sulfate, oxobis(1-phenyl-1,3-butanedionato)vanadium (IV), bis(maltolato)oxovanadium (IV), vanadium (V) pentoxide, sodium metavanadate (V), and ammonium metavanadate (V).

Examples of the halogen compounds that are suitable for use as the polymerization accelerator include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes that may be used as the polymerization accelerator include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde. Among these, p-n-octyloxybenzaldehyde is preferably used in view of curability.

Examples of the thiol compounds that may be used as the polymerization accelerator include 3-mercaptopropyltrimethoxysilane, 2-mercaptobenzoxazole, decanethiol, and thiobenzoic acid.

Examples of the sulfites that may be used as the polymerization accelerator include sodium sulfite, potassium sulfite, calcium sulfite, and ammonium sulfite.

Examples of the hydrogen sulfites that may be used as the polymerization accelerator include sodium hydrogen sulfite and potassium hydrogen sulfite.

Examples of the thiourea compounds that may be used as the polymerization accelerator include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

The dental bonding material (B) may contain a fluoride to the extent that the effect of the present invention does not become impaired. Any fluoride that is soluble in water and can release fluorine ion may be used. Specific examples of the fluoride include lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese (II) fluoride, iron (II) fluoride, iron (III) fluoride, cobalt (II) fluoride, copper (II) fluoride, zinc fluoride, antimony (III) fluoride, lead (II) fluoride, silver (I) fluoride, cadmium fluoride, tin (II) fluoride, tin (IV) fluoride, silver diamine fluoride, ammonium fluoride, sodium hydrogen fluoride, ammonium hydrogen fluoride, potassium hydrogen fluoride, sodium fluorophosphate, potassium hexafluorotitanate, sodium hexafluorosilicate, sodium hexafluorophosphate, sodium hexafluorostannate (IV), alanine hexafluorostannate (IV), sodium pentafluorostannate (II), and potassium hexafluorozirconate.

Depending on the embodiment employed, the dental bonding material (B) preferably further contains a filler. Fillers are typically classified broadly into an organic filler, an inorganic filler, and an organic-inorganic composite filler. Examples of the material of the organic filler include polymethyl methacrylate, polyethyl methacrylate, methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used alone or a mixture of two or more thereof may be used. The shape of the organic filler is not particularly limited, and the particle diameter of the filler used can be selected as appropriate. In view of the characteristics such as handling properties and mechanical strength of the resulting dental bonding material (B), the average particle diameter of the organic filler is preferably 0.001 to 50 µm and more preferably 0.001 to 10 µm.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone or a mixture of two or more thereof may be used. The shape of the inorganic filler is not particularly limited, and the particle diameter of the filler used can be selected as appropriate. In view of the characteristics such as handling properties and mechanical strength of the resulting dental bonding material (B), the average particle diameter of the inorganic filler is preferably 0.001 to 50 µm and more preferably 0.001 to 10 µm.

Examples of the shape of the inorganic filler include an irregular shape and a spherical shape. The inorganic filler used is preferably a spherical filler, in view of enhancement of the mechanical strength of the dental bonding material (B). The term "spherical filler" as used herein refers to a filler whose particles are rounded in shape as observed in a unit area of field of view in a photograph of the filler taken by a scanning electron microscope (which will hereinafter be abbreviated as "SEM") and have an average aspect ratio of 0.6 or more calculated as an average of values determined by dividing a diameter of each particle in a direction perpendicular to the maximum diameter of the particle by the maximum diameter. The average particle diameter of the spherical filler is preferably 0.1 to 5 µm. An average particle diameter less than 0.1 µm could cause a lower degree of filling of the dental bonding material (B) with the spherical filler and hence reduced mechanical strength. An average particle diameter more than 5 µm could cause a reduction in the surface area of the spherical filler, resulting in a failure to obtain a cured product having high mechanical strength.

The inorganic filler may be surface-treated beforehand with a commonly-known surface treatment agent such as a silane coupling agent where necessary in order to adjust the flowability of the dental bonding material (B). Examples of the surface treatment agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is obtainable by adding a monomer compound to the above inorganic filler, forming the mixture into a paste, then subjecting the paste to polymerization, and crushing the resulting polymer product. The organic-inorganic composite filler used can be, for example, a TMPT filler (obtainable by mixing trimethylolpropane methacrylate and a silica filler, subjecting the mixture to polymerization, and then crushing the resulting polymer product). The shape of the organic-inorganic composite filler is not particularly limited, and the particle diameter of the filler used can be selected as appropriate. In view of the characteristics such as handling properties and mechanical strength of the resulting dental bonding material (B), the average particle diameter of the organic-inorganic composite filler is preferably 0.001 to 50 µm and more preferably 0.001 to 10 µm. In the present invention, the average particle diameter of the filler can be determined by taking a photograph of the ultrafine particles of the filler with a scanning electron microscope (manufactured by Hitachi, Ltd., S-4000) and measuring the particle diameters of (200 or more) particles observed in a unit area of field of view in the photograph by the use of an image-analyzing particle size distribution analysis software (Macview manufactured by Mountech Co., Ltd.). The diameter of each particle is determined as a circle-equivalent diameter corresponding to the diameter of a circle having the same area as the particle. An average primary particle diameter is calculated from the number of particles and their particle diameters.

The content of the filler used in the present invention is not particularly limited. The content of the filler is preferably in the range of 0.1 to 30 weight %, more preferably in the range of 0.5 to 20 weight %, and most preferably in the range of 1 to 10 weight %, with respect to the total weight of the dental bonding material (B).

The dental bonding material (B) may contain a fluorine ion-releasing material to impart acid resistance to a tooth structure. Examples of the fluorine ion-releasing material include: fluorine glass materials such as fluoroaluminosilicate glass; metal fluorides such as sodium fluoride, potassium fluoride, sodium monofluorophosphate, lithium fluoride, and ytterbium fluoride; fluorine ion-releasing polymers such as a copolymer of methyl methacrylate and methacryloyl fluoride; and cetylamine hydrofluoride.

The dental bonding material (B) can contain a solvent according to a practical need. Examples of the solvent include water, an organic solvent, and a mixed solvent thereof.

The dental bonding material (B) containing water will promote the demineralizing action of the acid group-containing polymerizable monomer (A-1) on a tooth structure. The water used needs to be substantially free from impurities that adversely affect the bonding ability. The water is preferably distilled water or ion-exchanged water. Having too low a water content could lead to a failure to provide a sufficient promoting effect on the demineralizing action, while having too high a water content could cause reduced bonding ability. Thus, the water content is preferably in the range of 1 to 50 weight %, more preferably in the range of 5 to 30 weight %, and most preferably in the range of 10 to 20 weight %, with respect to the total weight of the dental bonding material (B).

The dental bonding material (B) containing an organic solvent will yield a further improvement in terms of bonding ability, coating properties, and penetration into tooth structures, and the organic solvent contained will prevent the components of the dental bonding material (B) from becoming separated from each other. The organic solvent used typically has a boiling point of 150° C. or lower at ordinary pressure and has a solubility of 5 weight % or more in water at 25° C. The organic solvent more preferably has a solubility of 30 weight % or more in water at 25° C. and is most preferably freely soluble in water at 25° C.

Examples of the organic solvent include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Among these, a water-soluble organic solvent is preferable as the organic solvent in view of both the safety for living organisms and the ease of removal utilizing volatility. To be specific, ethanol, 2-propanol, 2-methyl-2-propanol, acetone and tetrahydrofuran are preferably used. The content of the organic solvent is not particularly limited. Some embodiments have no need to contain the organic solvent. In embodiments using the organic solvent, the content of the organic solvent is preferably in the range of 1 to 70 weight %, more preferably in the range of 5 to 50 weight %, and most preferably in the range of 10 to 30 weight %, with respect to the total weight of the dental bonding material (B).

Furthermore, the dental bonding material (B) may contain, for example, a pH adjuster, a polymerization inhibitor, an ultraviolet absorber, a thickener, a colorant, a fluorescent agent, or a flavor to the extent that the effect of the present invention does not become impaired. Additionally, the dental bonding material (B) may contain an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan.

The dental adhesive kit of the present invention is a dental adhesive kit for bonding together a tooth structure and a restorative filling material such as a filling compomer or filling composite resin. The dental adhesive kit may be used also in combination with a luting material such as a resin cement, glass ionomer cement, zinc phosphate cement, polycarboxylate cement, silicate cement, or zinc oxide eugenol cement. Furthermore, the dental adhesive kit can be used by itself as a fissure sealant for pits and fissures, as a coating material for root surfaces and interproximal areas, or as a dentinal tubule sealant aimed at inhibition of hypersensitivity, without the use of a restorative filling material.

The dental adhesive kit can also be used for objects other than tooth structures, such as a metal, porcelain, and cured composite, and thus can be applied, for example, to a restorative material broken in an oral cavity. Furthermore, the dental adhesive kit may be used in combination with a commercially-available dental metal-adhesion primer, dental porcelain-adhesion primer, acid etching agent, or hypochlorite-containing tooth surface cleaning agent.

In the dental adhesive kit of the present invention, the bonding material has a good state stability and undergoes no deposition of the benzotriazole compound. The dental adhesive kit of the present invention has an excellent balance between photocurability for LED light irradiation and stability to ambient light. The dental adhesive kit exhibits high bond strengths to both enamel and dentin with small variability even when subjected to photocuring with a high-power LED irradiation device. Thus, the dental adhesive kit can constantly yield a certain level of bonding ability, which means that the dental adhesive kit has low sensitivity to the practitioner's technique. A typical method conventionally employed for bonding ability evaluation used to be tensile bond test. Nowadays, however, notched-edge shear test (which may be referred to as "Ultradent shear bond test" in the present description) has become widespread in Japan and foreign countries and is specified as a standard test in ISO. The dental adhesive kit of the present invention yields high bond strengths to both enamel and dentin in both the tensile bond test and the Ultradent shear bond test, even when subjected to short-time irradiation with a high-power LED irradiation device.

The present invention encompasses embodiments obtainable by combining the above features in various manners within the technical scope of the present invention as long as such embodiments exert the effect of the present invention.

EXAMPLES

The present invention will now be described in more detail by way of Examples. It should be noted that the present invention is not limited to Examples given below. Abbreviations used hereinafter are as follows.

[Dental Primer (A)]
[Acid Group-Containing Polymerizable Monomer (A-1)]
MDP: 10-methacryloyloxydecyl dihydrogen phosphate
[Hydrophilic Polymerizable Monomer (A-2)]
HEMA: 2-hydroxyethyl methacrylate
[Water (A-3)]
Purified water
[Polymerization Initiator]
CQ: Camphorquinone
DMAEMA: 2-(dimethylamino)ethyl methacrylate
[Dental Bonding Material (B)]
[Acid Group-Containing Polymerizable Monomer]
MDP: 10-methacryloyloxydecyl dihydrogen phosphate
MHP: 6-methacryloyloxyhexyl dihydrogen phosphate
[Hydrophilic Polymerizable Monomer (B-1)]
HEMA: 2-hydroxyethyl methacrylate
GLM: 2,3-dihydroxypropyl methacrylate
DEAA: N,N-diethylacrylamide
[Aromatic Bifunctional Polymerizable Monomer (B-2)]
Bis-GMA: 2,2-bis[4-(3-methacryloyloxy-2-hydroxypropoxy)phenyl]propane
3002M: "Epoxy Ester 3002M"
[Aliphatic Bifunctional Polymerizable Monomer (B-3)]
NPG: Neopentyl glycol dimethacrylate
3G: Triethylene glycol dimethacrylate
HD: 1,6-hexanediol dimethacrylate
DD: 1,10-decanediol dimethacrylate
[(Bis)Acylphosphine Oxide Compound (B-5)]
BAPO: Bis(2,4,6-trimethylbenzoyl)phenylphosphine oxide
TMDPO: 2,4,6-trimethylbenzoyldiphenylphosphine oxide
[Benzotriazole Compound (B-6)]
BNT1: 2-(3-t-butyl-5-methyl-2-hydroxyphenyl)-5-chlorobenzotriazole
BNT2: 2-(2'-hydroxy-5'-methylphenyl)benzotriazole
[Tertiary Amine]
DABE: Ethyl 4-(N,N-dimethylamino)benzoate
DEPT: N,N-di(2-hydroxyethyl)-p-toluidine
DMAEMA: 2-(dimethylamino)ethyl methacrylate
[Filler]
Inorganic filler 1: "AEROSIL (registered trademark) R972" manufactured by Nippon Aerosil Co., Ltd. (hydrophobic fumed silica having an average particle diameter of 16 nm)
Inorganic filler 2: "AEROSIL (registered trademark) Ar380" manufactured by Nippon Aerosil Co., Ltd. (particulate silica having an average particle diameter of 7 nm)
[Another Component]
BHT: 2,6-di-t-butyl-4-methylphenol (stabilizer (polymerization inhibitor))

Primers composed as shown in Table 1 were prepared. Bonding materials composed as shown in Tables 2 to 4 were prepared. The unit of the values presented for the components listed in the tables is parts by weight. The details of Examples and Comparative Examples will be given hereinafter, followed by a description of the methods for their evaluation.

Examples 1 to 4

Bonding materials were prepared by mixing MDP, HEMA, Bis-GMA, NPG, CQ, BAPO, DABE, DEPT, BHT, inorganic fillers, and BNT1 as the benzotriazole compound (B-6) at weight ratios shown in Table 2. These bonding materials were evaluated for the ambient light stability, photocuring time, and state stability according to the methods of the ambient light stability test, photocuring time measurement, and state stability test described later. Furthermore, bonding abilities achieved by combined use with the primer 1 (with the primer 2 in Example 3) were measured according to the methods of the tensile bond test and Ultradent shear bond test described later.

Example 5

A bonding material prepared using BNT2 as the benzotriazole compound (B-6) as shown in Table 2 was evaluated for the ambient light stability, photocuring time, and state stability, and examined for the tensile bond strength and Ultradent shear bond strength achieved by combined use with the primer 1.

Example 6

A bonding material prepared using GLM as the hydrophilic polymerizable monomer (B-1) as shown in Table 2 was evaluated for the ambient light stability, photocuring time, and state stability, and examined for the tensile bond strength and Ultradent shear bond strength achieved by combined use with the primer 1.

Example 7

A bonding material prepared using DEAA as the hydrophilic polymerizable monomer (B-1) as shown in Table 2 was evaluated for the ambient light stability, photocuring time, and state stability, and examined for the tensile bond strength and Ultradent shear bond strength achieved by combined use with the primer 1.

Example 8

A bonding material prepared using 3002M as the aromatic bifunctional polymerizable monomer (B-2) as shown in Table 2 was evaluated for the ambient light stability, photocuring time, and state stability, and examined for the tensile bond strength and Ultradent shear bond strength achieved by combined use with the primer 1.

Example 9

A bonding material prepared using 3G as the aliphatic bifunctional polymerizable monomer (B-3) as shown in Table 2 was evaluated for the ambient light stability, photocuring time, and state stability, and examined for the tensile bond strength and Ultradent shear bond strength achieved by combined use with the primer 1.

Example 10

A bonding material prepared using HD as the aliphatic bifunctional polymerizable monomer (B-3) as shown in Table 2 was evaluated for the ambient light stability, photocuring time, and state stability, and examined for the tensile bond strength and Ultradent shear bond strength achieved by combined use with the primer 1.

Example 11

A bonding material prepared using DD as the aliphatic bifunctional polymerizable monomer (B-3) as shown in Table 2 was evaluated for the ambient light stability, photocuring time, and state stability, and examined for the tensile bond strength and Ultradent shear bond strength achieved by combined use with the primer 1.

Example 12

A bonding material prepared using MHP as the acid group-containing polymerizable monomer as shown in Table 2 was evaluated for the ambient light stability, photocuring time, and state stability, and examined for the tensile bond strength and Ultradent shear bond strength achieved by combined use with the primer 1.

Example 13

A bonding material containing no MDP as shown in Table 2 was evaluated for the ambient light stability, photocuring time, and state stability, and examined for the tensile bond strength and Ultradent shear bond strength achieved by combined use with the primer 1.

Example 14

A bonding material prepared using TMDPO as the (bis) acylphosphine oxide compound (B-5) as shown in Table 2 was evaluated for the ambient light stability, photocuring time, and state stability, and examined for the tensile bond strength and Ultradent shear bond strength achieved by combined use with the primer 1.

Examples 15 to 18

Bonding materials were prepared by mixing MDP, HEMA, Bis-GMA, NPG, CQ, BAPO, DABE, DEPT, BNT1, BHT, and inorganic fillers at weight ratios shown in Table 3. The bonding materials were evaluated for the ambient light stability, photocuring time, and state stability, and examined for the tensile bond strength and Ultradent shear bond strength achieved by combined use with the primer 1.

Comparative Example 1

A bonding material containing no benzotriazole compound (B-6) as shown in Table 4 was evaluated for the ambient light stability, photocuring time, and state stability, and examined for the tensile bond strength and Ultradent shear bond strength achieved by combined use with the primer 1.

Comparative Example 2

A bonding material prepared using NPG as the aliphatic bifunctional polymerizable monomer (B-3) and containing 0.75 parts by weight of the benzotriazole compound (B-6) as shown in Table 4 was evaluated for the ambient light stability, photocuring time, and state stability, and examined for the tensile bond strength and Ultradent shear bond strength achieved by combined use with the primer 1.

Comparative Example 3

A bonding material prepared using 3G as the aliphatic bifunctional polymerizable monomer (B-3) and containing 0.75 parts by weight of the benzotriazole compound (B-6) as shown in Table 4 was evaluated for the ambient light stability, photocuring time, and state stability, and examined for the tensile bond strength and Ultradent shear bond strength achieved by combined use with the primer 1.

Comparative Example 4

A bonding material containing no benzotriazole compound (B-6) and containing 0.4 parts by weight of the α-diketone compound per part by weight of the acylphosphine oxide compound as shown in Table 4 was evaluated for the ambient light stability, photocuring time, and state stability, and examined for the tensile bond strength and Ultradent shear bond strength achieved by combined use with the primer 1.

[Ambient Light Stability Test]

In a dark room under light of a xenon lamp having a color temperature conversion film and an ultraviolet filter inserted therein, a mixing dish (manufactured by Kuraray Noritake Dental Inc., Product No. "#912 (TB)") was placed at a height where the illuminance was 8000 lux. A single drop of bonding material was put on the mixing dish. The sample was exposed to light for a predetermined period of time. Then, the mixing dish on which was put the drop of the sample was taken out of the illuminated area, and the sample was immediately inspected for its physical homogeneity. The length of time during which the sample maintained homogeneity was determined as the allowable operation time.

In general, a bonding material for use in a two-step adhesive system, which requires only a relatively short time for processing, can be used for clinical purposes without any problem insofar as the bonding material offers an allowable operation time of 20 seconds or longer under ambient light. The allowable operation time under ambient light is more preferably 25 seconds or more and most preferably 30 seconds or more.

[Photocuring Time Measurement Method]

A drop of bonding material weighing 0.015 g was put inside a 4-mm-diameter hole of a washer bonded to a prepared glass slide. A thermocouple (manufactured by Okazaki Manufacturing Company under the product code "SKC/C") connected to a recorder (manufactured by Yokogawa Electric Corporation under the product code "Type 3066") was dipped in the bonding material placed inside the washer, and the bonding material was irradiated with light through the under surface of the prepared slide using a dental LED light irradiation device (manufactured by Morita Corporation under the trade name "PenCure 2000"). The time from the start of the light irradiation to the appearance of exothermic peak top resulting from curing was determined as the photocuring time (seconds).

[State Stability]

Bonding materials that showed no particular defective state after preparation were left in a cold storage chamber (at 2 to 8° C.) for 3 months. Afterwards, the bonding materials were taken out of the chamber, allowed to attain an ordinary temperature, and evaluated for stability based on state changes such as deposition. The state stability was rated as "Good" for bonding materials that underwent no observable deposition and no change from the as-prepared state, while the state stability was rated as "Poor" for bonding materials that clearly showed deposition.

[Tensile Bond Test]

The labial surfaces of bovine mandibular incisors were each ground with #80 silicon carbide paper (manufactured by Nihon Kenshi Co., Ltd.) under running water to obtain samples with an exposed flat enamel surface and samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was delimited.

A prepared sample primer was applied within the circular hole with a brush and left for 20 seconds, after which the applied primer was dried by subjecting its surface to air-blowing until the primer lost its flowability. Next, a bonding material was applied over the primer applied and dried on the tooth surface. Subsequently, the applied primer and bonding material were cured by 10-second light irradiation (referred to as "normal irradiation") with a dental light irradiation device (manufactured by Morita Corporation under the trade name "PenCure 2000") set in normal mode or by 3-second light irradiation (referred to as "short-time irradiation") with the dental light irradiation device set in high-power mode.

To the surface of the obtained cured product of the bonding material was applied a dental filling composite resin (manufactured by Kuraray Noritake Dental Inc. under the trade name "CLEARFIL AP-X" (registered trademark)), which was covered with a release film (made of polyester). Next, a glass slide was placed on and pressed against the release film to flatten the surface of the applied composite resin. Subsequently, the composite resin was cured by subjecting the resin to 20-second irradiation through the release film using the irradiation device "PenCure 2000" set in normal mode or by subjecting the resin to 3-second light irradiation (short-time irradiation) twice through the release film using the irradiation device set in high-power mode.

Using a commercially-available dental resin cement (manufactured by Kuraray Medical Inc. under the trade name "PANAVIA 21" (registered trademark)), a cylindrical stainless steel rod (with a diameter of 7 mm and a length of 2.5 cm) was bonded at its one end face (circular end face) to the surface of the obtained cured product of the dental filling composite resin. Thus, a test specimen was prepared. A total of 20 such test specimens (10 specimens with an exposed enamel surface and 10 specimens with an exposed dentin surface) were prepared. Next, each test specimen immersed in distilled water held in a sample container was left in a thermostat set at 37° C. for 24 hours, after which the test specimen was taken out and measured for bond strength. The bond strength (tensile bond strength) measurement was performed using a universal testing machine (manufactured by Shimadzu Corporation) with the crosshead speed set at 2 mm/minute. An average of the measured values of the 10 test specimens was employed as the value of the bond strength.

For the samples subjected to the short-time irradiation, a coefficient of variation was determined as a measure of their technique sensitivity. The coefficient of variation is a coefficient of variation [standard deviation (σ)/average] defined in JIS Z 8101-1 (1999). A smaller coefficient of variation of the bond strength of a material indicates that the material has lower sensitivity to the practitioner's technique and can constantly exhibit a certain level of bonding ability with less variability.

A material showing a coefficient of variation of 0.3 or less can be determined to have low technique sensitivity. The coefficient of variation is more preferably 0.25 or less.

[Ultradent Shear Bond Test]

The labial surfaces of bovine mandibular incisors were each ground with #80 silicon carbide paper (manufactured by Nihon Kenshi Co., Ltd.) under running water to obtain samples with an exposed flat enamel surface and samples with an exposed flat dentin surface. Each sample tooth was fixed on a tape attached to the bottom surface of a 15-hole mold (manufactured by Ultradent Products, Inc. and having a diameter of 35 mm and a height of 25 mm). Plaster was loaded into the mold and left for about 30 minutes to allow the plaster to cure. The sample was removed from the mold and ground with #600 silicon carbide paper (manufactured by Nihon Kenshi Co., Ltd.) under running water to a size (diameter of 2.38 mm or more) which allows the provision of an adherend surface. The sample was then washed with water under ultrasonic wave for 5 minutes.

A primer was applied to the adherent surface of the sample with a brush and left for 20 seconds, after which the applied primer was dried by subjecting its surface to air-blowing until the primer lost its flowability. Next, the bonding material was applied over the primer applied and dried on the tooth surface. Subsequently, the applied primer and bonding material were cured by 10-second light irradiation with a dental LED light irradiation device (manufactured by Morita Corporation under the trade name "Pen-Cure 2000") set in normal mode.

A mold for CR filling with a diameter of 2.38 mm (BONDING MOLD INSERT, manufactured by Ultradent Products, Inc.) was mounted to a dedicated instrument (BONDING CLAMP, manufactured by Ultradent Products, Inc.). The mold was moved down to the position of the processed primer and bonding material and brought into close contact with the adherend surface. A composite resin for dental filling (manufactured by Kuraray Noritake Dental Inc. under the trade name "CLEARFIL AP-X" (registered trademark)) was put into the hole of the mold and spread to a small thickness of 1 mm or less. Afterwards, AP-X was further put into the mold (to a total thickness of about 1.5 mm, which corresponded to about ¾ of the height of the mold). The AP-X was subjected to 20-second light irradiation with the irradiation device "PenCure 2000" set in normal mode. The sample was removed from the mold and used as a test specimen. In this manner, a total of 20 such test specimens (10 specimens with an exposed enamel surface and 10 specimens with an exposed dentin surface) were prepared. Next, each test specimen immersed in distilled water held in a sample container was left in a thermostat set at 37° C. for 24 hours, after which the test specimen was taken out and measured for bond strength. The bond strength (shear bond strength) measurement was performed on each test specimen attached to a dedicated holder (TEST BASE CLAMP, manufactured by Ultradent Products, Inc.) using a dedicated jig (CROSSHEAD ASSEMBLY, manufactured by Ultradent Products, Inc.) and a universal testing machine (manufactured by Shimadzu Corporation) with the crosshead speed set at 1 mm/minute. An average of the measured values of the 10 test specimens was employed as the value of the bond strength.

TABLE 1

| Components (Unit: parts by weight) | | Primer 1 | Primer 2 |
|---|---|---|---|
| Acid group-containing polymerizable monomer (A-1) | MDP | 15 | 15 |
| Hydrophilic polymerizable monomer (A-2) | HEMA | 40 | 40 |
| Water (A-3) | Water | 45 | 45 |
| Polymerization initiator | CQ | 0.3 | — |
| | DMAEMA | 0.5 | — |

TABLE 2

| Components (Unit: parts by weight) | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Acid group-containing polymerizable monomer | MDP | 5 | 5 | 5 | 5 | 5 | 5 | 5 | 5 | 5 | 5 |
| Hydrophilic polymerizable monomer (B-1) | HEMA | 40 | 40 | 40 | 40 | 40 | | | 40 | 40 | 40 |
| | GLM | | | | | | 40 | | | | |
| | DEAA | | | | | | | 40 | | | |
| Aromatic bifunctional polymerizable monomer (B-2) | Bis-GMA | 40 | 40 | 40 | 40 | 40 | 40 | 40 | | 40 | 40 |
| | 3002M | | | | | | | | 40 | | |
| Aliphatic bifunctional polymerizable monomer (B-3) | NPG | 20 | 20 | 20 | 20 | 20 | 20 | 20 | 20 | | |
| | 3G | | | | | | | | | 20 | |
| | HD | | | | | | | | | | 20 |
| α-diketone (B-4) | CQ | 0.8 | 0.8 | 0.8 | 0.8 | 0.8 | 0.8 | 0.8 | 0.8 | 0.8 | 0.8 |
| (Bis)acylphosphine oxide compound (B-5) | BAPO | 1.0 | 1.0 | 1.0 | 1.0 | 1.0 | 1.0 | 1.0 | 1.0 | 1.0 | 1.0 |
| Tertiary amine | DABE | 2.0 | 2.0 | 2.0 | 2.0 | 2.0 | 2.0 | 2.0 | 2.0 | 2.0 | 2.0 |
| | DEPT | 0.5 | 0.5 | 0.5 | 0.5 | 0.5 | 0.5 | 0.5 | 0.5 | 0.5 | 0.5 |
| Benzotriazole compound (B-6) | BNT1 | 0.15 | 0.3 | 0.3 | 0.5 | | 0.3 | 0.3 | 0.3 | 0.3 | 0.3 |
| | BNT2 | | | | | 0.3 | | | | | |
| Another component | BHT | 0.05 | 0.05 | 0.05 | 0.05 | 0.05 | 0.05 | 0.05 | 0.05 | 0.05 | 0.05 |
| Filler | Inorganic filler 1 | 8.0 | 8.0 | 8.0 | 8.0 | 8.0 | 8.0 | 8.0 | 8.0 | 8.0 | 8.0 |
| | Inorganic filler 2 | 1.5 | 1.5 | 1.5 | 1.5 | 1.5 | 1.5 | 1.5 | 1.5 | 1.5 | 1.5 |
| Ambient light stability (seconds) under 8000 lux | | 25 | 30 | 30 | 35 | 25 | 30 | 25 | 30 | 30 | 30 |
| Photocuring time (seconds) | | 6.8 | 6.8 | 6.8 | 6.9 | 6.7 | 6.7 | 6.6 | 6.9 | 6.6 | 6.4 |
| State stability | | Good | Good | Good | Good | Good | Good | Good | Good | Good | Good |
| Bond strength (MPa) | Primer used in combination | Primer 1 | | Primer 2 | | | | | Primer 1 | | |
| | Tensile bond strength (Normal irradiation) Enamel | 22.6 | 23.1 | 22.4 | 23.3 | 21.8 | 22.1 | 21.7 | 22.6 | 22.5 | 20.7 |
| | Dentin | 21.2 | 21.5 | 20.6 | 20.7 | 20.6 | 20.8 | 20.6 | 20.9 | 20.5 | 19.8 |
| | Tensile bond strength Enamel | 21.2 | 20.7 | 20.4 | 21.1 | 20.7 | 20.6 | 20.4 | 20.3 | 21.1 | 20.6 |

TABLE 2-continued

| Components (Unit: parts by weight) | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| (Short-time irradiation) | Coefficient of variation | 0.21 | 0.18 | 0.18 | 0.24 | 0.24 | 0.23 | 0.21 | 0.21 | 0.23 | 0.19 |
| | Dentin | 19.6 | 19.4 | 18.9 | 19.3 | 19.1 | 19.3 | 18.8 | 18.7 | 18.3 | 18.2 |
| | Coefficient of variation | 0.19 | 0.22 | 0.21 | 0.23 | 0.24 | 0.22 | 0.23 | 0.23 | 0.24 | 0.24 |
| Ultradent shear bond strength | Enamel | 42.4 | 43.2 | 41.1 | 42.7 | 41.4 | 42.2 | 41.7 | 41.9 | 40.3 | 39.9 |
| | Dentin | 50.8 | 51.3 | 50.1 | 50.3 | 50.2 | 50.6 | 50.2 | 51.0 | 48.5 | 48.2 |

TABLE 3

| Components (Unit: parts by weight) | | Example 11 | Example 12 | Example 13 | Example 14 | Example 15 | Example 16 | Example 17 | Example 18 |
|---|---|---|---|---|---|---|---|---|---|
| Acid group-containing polymerizable monomer | MDP | 5 | | | 5 | 5 | 5 | 5 | 5 |
| | MHP | | 5 | | | | | | |
| Hydrophilic polymerizable monomer (B-1) | HEMA | 40 | 40 | 40 | 40 | 40 | 30 | 50 | 30 |
| Aromatic bifunctional polymerizable monomer (B-2) | Bis-GMA | 40 | 40 | 40 | 40 | 40 | 50 | 30 | 30 |
| Aliphatic bifunctional polymerizable monomer (B-3) | NPG | | 20 | 20 | 20 | 20 | 15 | 15 | 25 |
| | DD | 20 | | | | | | | |
| α-diketone (B-4) | CQ | 0.8 | 0.8 | 0.8 | 1.2 | 0.9 | 0.8 | 0.8 | 0.8 |
| (Bis)acylphosphine oxide compound (B-5) | BAPO | 1.0 | 1.0 | 1.0 | | 0.5 | 1.0 | 1.0 | 1.0 |
| | TMDPO | | | | 2.0 | | | | |
| Tertiary amine | DABE | 2.0 | 2.0 | 2.0 | 2.0 | 2.0 | 2.0 | 2.0 | 2.0 |
| | DEPT | 0.5 | 0.5 | 0.5 | 0.5 | 0.5 | 0.5 | 0.5 | 0.5 |
| Benzotriazole compound (B-6) | BNT1 | 0.3 | 0.3 | 0.3 | 0.3 | 0.3 | 0.3 | 0.3 | 0.3 |
| Another component | BHT | 0.05 | 0.05 | 0.05 | 0.05 | 0.05 | 0.05 | 0.05 | 0.05 |
| Filler | Inorganic filler 1 | 8.0 | 8.0 | 8.0 | 8.0 | 8.0 | 8.0 | 8.0 | 8.0 |
| | Inorganic filler 2 | 1.5 | 1.5 | 1.5 | 1.5 | 1.5 | 1.5 | 1.5 | 1.5 |
| Ambient light stability (seconds) under 8000 lux | | 30 | 30 | 25 | 30 | 25 | 30 | 25 | 35 |
| Photocuring time (seconds) | | 7.3 | 7.1 | 7.4 | 8.3 | 7.0 | 6.8 | 7.1 | 6.6 |
| State stability | | Good | Good | Good | Good | Good | Good | Good | Good |
| Bond strength (MPa) | Primer used in combination | | | | Primer 1 | | | | |
| | Tensile bond strength (Normal irradiation) Enamel | 21.4 | 21.8 | 22.5 | 20.2 | 21.6 | 21.3 | 22.1 | 21.8 |
| | Dentin | 19.7 | 21.1 | 21.4 | 18.6 | 20.8 | 20.7 | 21.1 | 20.5 |
| | Tensile bond strength (Short-time irradiation) Enamel | 20.8 | 20.7 | 21.4 | 19.7 | 20.4 | 20.6 | 20.9 | 20.4 |
| | Coefficient of variation | 0.21 | 0.21 | 0.22 | 0.26 | 0.22 | 0.23 | 0.21 | 0.23 |
| | Dentin | 18.3 | 19.1 | 18.9 | 17.4 | 18.9 | 19.1 | 19.4 | 19.7 |
| | Coefficient of variation | 0.21 | 0.22 | 0.21 | 0.26 | 0.21 | 0.23 | 0.20 | 0.21 |
| | Ultradent shear bond strength Enamel | 40.1 | 41.5 | 41.6 | 38.4 | 41.3 | 40.8 | 40.6 | 41.4 |
| | Dentin | 48.3 | 49.7 | 50.1 | 46.6 | 50.1 | 50.4 | 50.7 | 50.8 |

TABLE 4

| Components (Unit: parts by weight) | | Comp. Example 1 | Comp. Example 2 | Comp. Example 3 | Comp. Example 4 |
|---|---|---|---|---|---|
| Acid group-containing polymerizable monomer | MDP | 5 | 5 | 5 | 5 |
| Hydrophilic polymerizable monomer (B-1) | HEMA | 40 | 40 | 40 | 40 |
| Aromatic bifunctional polymerizable monomer (B-2) | Bis-GMA | 40 | 40 | 40 | 40 |
| Aliphatic bifunctional polymerizable monomer (B-3) | NPG | 20 | 20 | | 20 |
| | 3G | | | 20 | |
| α-diketone (B-4) | CQ | 0.8 | 0.8 | 0.8 | 0.4 |
| (Bis)acylphosphine oxide compound (B-5) | BAPO | 1 | 1 | 1 | 1 |
| Aromatic tertiary amine | DABE | 2 | 2 | 2 | 2 |
| | DEPT | 0.5 | 0.5 | 0.5 | 0.5 |
| Benzotriazole compound (B-6) | BNT1 | | 0.75 | 0.75 | |
| Another component | BHT | 0.05 | 0.05 | 0.05 | 0.05 |
| Filler | Inorganic filler 1 | 8 | 8 | 8 | 8 |
| | Inorganic filler 2 | 1.5 | 1.5 | 1.5 | 1.5 |
| Ambient light stability (seconds) under 8000 lux | | 15 | 35 | 35 | 25 |
| Photocuring time (seconds) | | 6.7 | 7.1 | 7.2 | 8.6 |
| State stability | | Good | Poor | Poor | Good |

TABLE 4-continued

| Components (Unit: parts by weight) | | | Comp. Example 1 | Comp. Example 2 | Comp. Example 3 | Comp. Example 4 |
|---|---|---|---|---|---|---|
| Bond strength (MPa) | Primer used in combination | | Primer 1 | | | |
| | Tensile bond strength (Normal irradiation) | Enamel | 22.6 | 23.1 | 23.3 | 19.8 |
| | | Dentin | 21.2 | 21.5 | 20.7 | 17.3 |
| | Tensile bond strength (Short-time irradiation) | Enamel | 21.9 | 20.5 | 20.7 | 18.4 |
| | | Coefficient of variation | 0.21 | 0.23 | 0.23 | 0.32 |
| | | Dentin | 19.3 | 18.8 | 18.4 | 16 |
| | | Coefficient of variation | 0.19 | 0.22 | 0.24 | 0.41 |
| | Ultradent shear bond strength | Enamel | 41.7 | 42.1 | 41.3 | 37.2 |
| | | Dentin | 51.4 | 50.7 | 48.2 | 41.1 |

Tables 2 and 3 show that the bonding materials (Examples 1 to 14) corresponding to that of the dental adhesive kit according to the present invention have excellent ambient light stability by virtue of containing a benzotriazole compound as an ambient light stabilizer. Besides, there is no extension of the photocuring time caused by the addition of the compound, and bonding abilities exhibited in the tensile bond strength test are excellent for both enamel and dentin, whichever of normal irradiation and short-time irradiation is employed. Bonding abilities exhibited in the Ultradent shear bond strength test are also high. By contrast, Table 4 demonstrates that the bonding material containing no benzotriazole compound (Comparative Example 1) has poor ambient light stability, and that the bonding materials containing 0.75 parts by weight of a benzotriazole compound, i.e., the bonding materials containing 3.75 parts by weight of a benzotriazole compound per 100 parts by weight of the aliphatic bifunctional polymerizable monomer (B-3) (Comparative Examples 2 and 3) have poor state stability and undergo deposition of the benzotriazole compound after storage for a certain period of time. It can also be found that the bonding material containing 0.4 parts by weight of an α-diketone compound per part by weight of a (bis)acylphosphine oxide compound (Comparative Example 4) shows low bonding ability, great variability in bond strength as demonstrated by the high coefficient of variation, and a low Ultradent shear bond strength, when subjected to short-time irradiation with a high-power LED irradiation device.

INDUSTRIAL APPLICABILITY

The dental adhesive kit according to the present invention including a dental primer and a dental bonding material can be suitably used in dentistry to bond together a hard tissue (tooth structure) of a tooth and a dental restorative material such as a dental composite resin, dental compomer, or dental resin cement.

The invention claimed is:

1. A dental adhesive kit, comprising:
a dental primer (A); and
a dental bonding material (B),
wherein
the dental primer (A) comprises an acid group-containing polymerizable monomer (A-1), a hydrophilic polymerizable monomer (A-2), and water (A-3),
the dental bonding material (B) comprises a hydrophilic polymerizable monomer (B-1), an aromatic bifunctional polymerizable monomer (B-2), an aliphatic bifunctional polymerizable monomer (B-3), an α-diketone compound (B-4), a (bis)acylphosphine oxide compound (B-5), and a benzotriazole compound (B-6) of the formula (1):

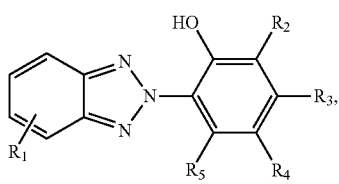

(1)

where $R_1$ is a hydrogen atom, a halogen atom, or an alkyl group having 1 to 6 carbon atoms, and $R_2$ to $R_5$ are each independently a hydrogen atom, a halogen atom, or an organic group having 1 to 12 carbon atoms and optionally containing at least one atom selected from the group consisting of an oxygen atom, a nitrogen atom, a sulfur atom, and a phosphorus atom, a content of the α-diketone compound (B-4) is 0.6 to 2 parts by weight per one part by weight of the (bis) acylphosphine oxide compound (B-5), and a content of the benzotriazole compound (B-6) is 0.01 to 3 parts by weight per 100 parts by weight of the aliphatic bifunctional polymerizable monomer (B-3).

2. The dental adhesive kit according to claim 1, wherein the (bis)acylphosphine oxide compound (B-5) is a bisacylphosphine oxide compound.

3. The dental adhesive kit according to claim 1, wherein a content of the hydrophilic polymerizable monomer (B-1) is 10 to 70 weight %, a content of the aromatic bifunctional polymerizable monomer (B-2) is 10 to 70 weight %, and a content of the aliphatic bifunctional polymerizable monomer (B-3) is 5 to 50 weight %, with respect to the total weight of the dental bonding material (B).

4. The dental adhesive kit according to claim 2, wherein a content of the hydrophilic polymerizable monomer (B-1) is 10 to 70 weight %, a content of the aromatic bifunctional polymerizable monomer (B-2) is 10 to 70 weight %, and a content of the aliphatic bifunctional polymerizable monomer (B-3) is 5 to 50 weight %, with respect to the total weight of the dental bonding material (B).

5. The dental adhesive kit according to claim 1, wherein the hydrophilic polymerizable monomer (B-1) comprises at least one selected from the group consisting of 2-hydroxyethyl (meth)acrylate, glycerin mono(meth)acrylate, and N,N-diethyl(meth)acrylamide.

6. The dental adhesive kit according to claim 1, wherein the aromatic bifunctional polymerizable monomer (B-2) comprises at least one selected from the group consisting of 2,2-bis[4-(3-methacryloyloxy-2-hydroxypropoxy)phenyl] propane and a compound represented by the formula (A):

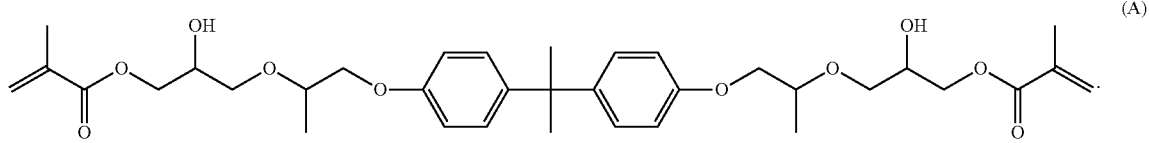 [SMILES: C=C(C)C(=O)OCC(O)COC(C)COc1ccc(C(C)(C)c2ccc(OCC(C)OCC(O)COC(=O)C(=C)C)cc2)cc1]

7. The dental adhesive kit according to claim 1, wherein the aliphatic bifunctional polymerizable monomer (B-3) comprises at least one selected from the group consisting of neopentyl glycol di(meth)acrylate, triethylene glycol di(meth)acrylate, 1,6-hexanediol di(meth)acrylate, and 1,10-decanediol di(meth)acrylate.

8. The dental adhesive kit according to claim 1, wherein the α-diketone compound (B-4) comprises at least one selected from the group consisting of diacetyl, dibenzyl, camphorquinone, 2,3-pentadione, 2,3-octadione, 9,10-phenanthrenequinone, 4,4'-oxybenzyl, and acenaphthenequinone.

9. The dental adhesive kit according to claim 1, wherein the dental primer (A) further comprises a polymerization initiator.

10. The dental adhesive kit according to claim 1, wherein the hydrophilic polymerizable monomer (B-1) is included in the dental bonding material (B) in an amount of from 15 to 60 weight % with respect to the total weight of the dental bonding material (B).

11. The dental adhesive kit according to claim 1, wherein the aromatic bifunctional polymerizable monomer (B-2) is included in the dental bonding material (B) in an amount of from 15 to 60 weight % with respect to the total weight of the dental bonding material (B).

12. The dental adhesive kit according to claim 1, wherein the aliphatic bifunctional polymerizable monomer (B-3) is included in the dental bonding material (B) in an amount of from 7 to 45 weight % with respect to the total weight of the dental bonding material (B).

13. The dental adhesive kit according to claim 1, wherein the α-diketone compound (B-4) and the (bis)acylphosphine oxide compound (B-5) are included in the dental bonding material (B) in a total of from 0.5 to 5 weight % with respect to the total weight of the dental bonding material (B).

14. The dental adhesive kit according to claim 1, wherein the dental bonding material (B) further comprises a filler having an average particle diameter of from 0.001 μm to 50 μm.

15. The dental adhesive kit according to claim 1, wherein the content of the α-diketone compound (B-4) is 0.6 to 1.8 parts by weight per one part by weight of the (bis)acylphosphine oxide compound (B-5).

16. The dental adhesive kit according to claim 1, wherein the content of the benzotriazole compound (B-6) is 0.75 to 3 parts by weight per 100 parts by weight of the aliphatic bifunctional polymerizable monomer (B-3).

17. The dental adhesive kit according to claim 1, wherein the acid group-containing polymerizable monomer (A-1) is included in the dental primer (A) in an amount of from 1 to 50 weight % with respect to the total weight of the dental primer (A).

18. The dental adhesive kit according to claim 1, wherein the hydrophilic polymerizable monomer (A-2) is included in the dental primer (A) in an amount of from 0.1 to 95 weight % with respect to the total weight of the dental primer (A).

19. The dental adhesive kit according to claim 1, wherein the water (A-3) is included in the dental primer (A) in an amount of from 0.01 to 90 weight % with respect to the total weight of the dental primer (A).

20. The dental adhesive kit according to claim 3,
wherein the hydrophilic polymerizable monomer (B-1) comprises at least one selected from the group consisting of 2-hydroxyethyl (meth)acrylate, glycerin mono (meth)acrylate, and N,N-diethyl(meth)acrylamide,
the aromatic bifunctional polymerizable monomer (B-2) comprises at least one selected from the group consisting of 2,2-bis[4-(3-methacryloyloxy-2-hydroxypropoxy)phenyl]propane and a compound represented by the formula (A):

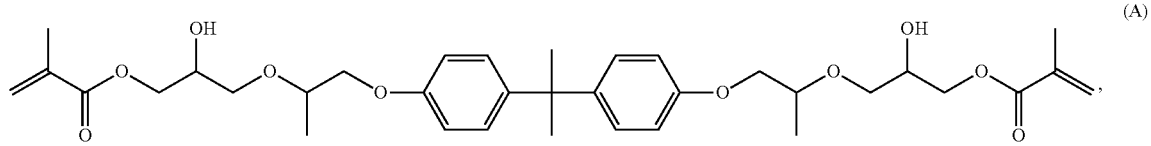

the aliphatic bifunctional polymerizable monomer (B-3) comprises at least one selected from the group consisting of neopentyl glycol di(meth)acrylate, triethylene glycol di(meth)acrylate, 1,6-hexanediol di(meth)acrylate, and 1,10-decanediol di(meth)acrylate, the α-diketone compound (B-4) comprises at least one selected from the group consisting of diacetyl, dibenzyl, camphorquinone, 2,3-pentadione, 2,3-octadione, 9,10-phenanthrenequinone, 4,4'-oxybenzyl, and acenaphthenequinone, and the (bis)acylphosphine oxide compound (B-5) is a bisacylphosphine oxide compound.

* * * * *